US00PP28885P3

(12) United States Plant Patent
Fabre

(10) Patent No.: US PP28,885 P3
(45) Date of Patent: Jan. 23, 2018

(54) APPLE TREE NAMED 'GALAFAB'

(50) Latin Name: ***Malus domestica* Borkh**
Varietal Denomination: Galafab

(71) Applicant: Lionel Fabre, Entraigues (FR)

(72) Inventor: Lionel Fabre, Entraigues (FR)

( * ) Notice: Subject to any disclaimer, the term of this patent is extended or adjusted under 35 U.S.C. 154(b) by 45 days.

(21) Appl. No.: 13/999,856

(22) Filed: Mar. 28, 2014

(65) Prior Publication Data

US 2015/0282400 P1 Oct. 1, 2015

(51) Int. Cl.
*A01H 5/08* (2006.01)

(52) U.S. Cl.
USPC ..... Plt./162

(58) Field of Classification Search
USPC ..... Plt./162, 161
CPC ..... A01H 5/0875; A01H 5/08; A01H 5/0831
See application file for complete search history.

*Primary Examiner* — June Hwu
(74) *Attorney, Agent, or Firm* — Michelle Bos Legal LLC

(57) ABSTRACT

'Galafab' is a new and distinct variety of apple tree (*Malus domestica* Borkh). A mutation of 'Gala' (not patented), 'Galafab' is characterized by its intense red overcolor.

4 Drawing Sheets

Latin name: *Malus domestica* Borkh.
Common name: Apple.
Variety denomination: 'Galafab'.

CROSS REFERENCE TO RELATED APPLICATIONS

None

BACKGROUND OF THE VARIETY

'Galafab' is a new and distinct variety of apple tree *Malus domestica* Borkh. This new variety is a limb-sport mutation of 'Gala' (not patented), and is characterized by its intense red overcolor. 'Galafab' was first observed in a cultivated orchard at Athens les Paluds, France in 2008, and was asexually reproduced by grafting at the same location in 2009. The variety has been observed to remain true to type over successive asexually propagated generations.

BRIEF DESCRIPTION OF THE VARIETY

'Galafab' was first selected for its uniquely colored fruit. It is distinguished from 'Gala' by its intense red overcolor, as set forth in the Table 1:

TABLE 1

Comparison of 'Galafab' to 'Gala'

| Characteristic | 'Galafab' | 'Gala' |
|---|---|---|
| Relative area of over color | Very large | Medium |
| Pattern of over color | Solid flush with strongly defined stripes | Large stripes |

'Galafab' is distinguished from 'Galaxy' gala (U.S. Plant Pat. No. 6,955), a similar variety, as set forth in Table 2:

TABLE 2

Comparison of 'Galafab' to 'Galaxy'

| Characteristic | 'Galafab' | 'Galaxy' |
|---|---|---|
| Stripes | No stripes | Striped |
| Relative area of overcolor | 100% | 72% |
| Intensity of overcolor | More intense | Less intense |

BRIEF DESCRIPTION OF THE PHOTOGRAPHS

Figure 1:
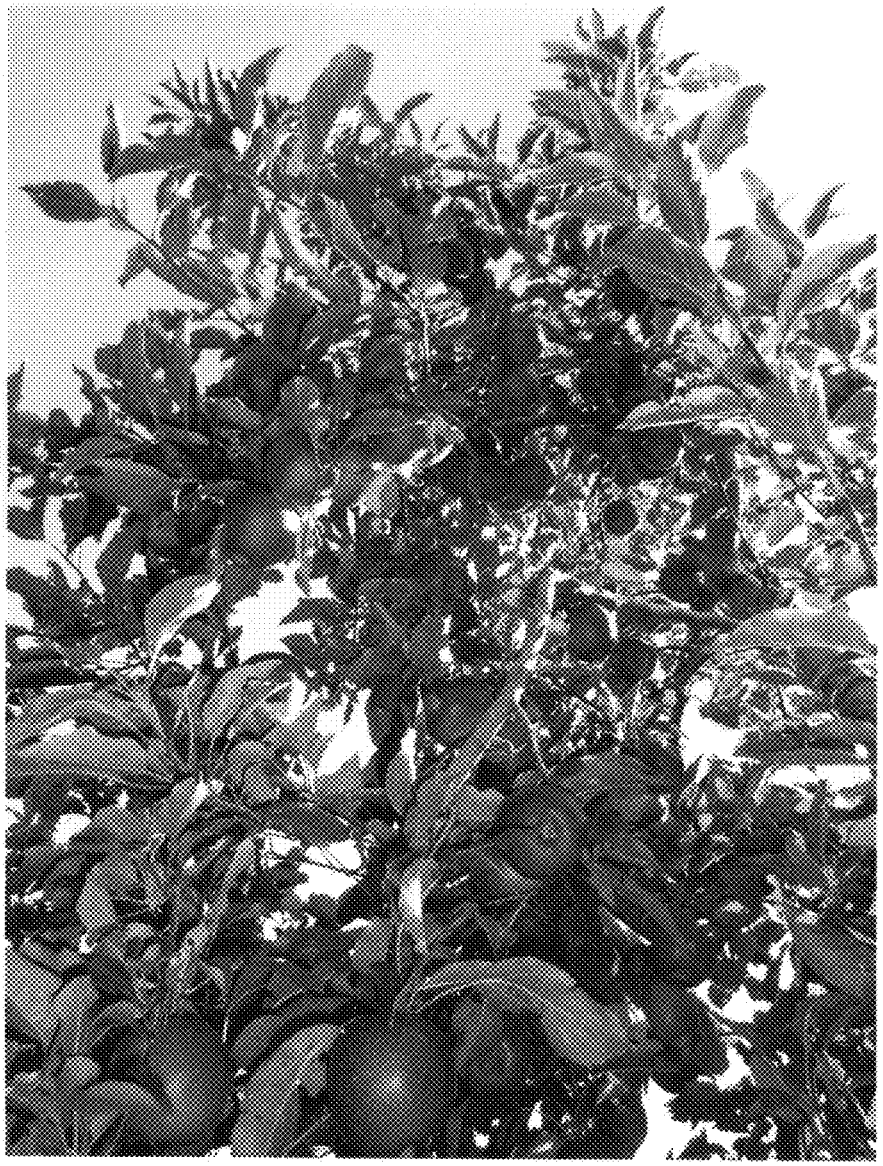
Figure 2:
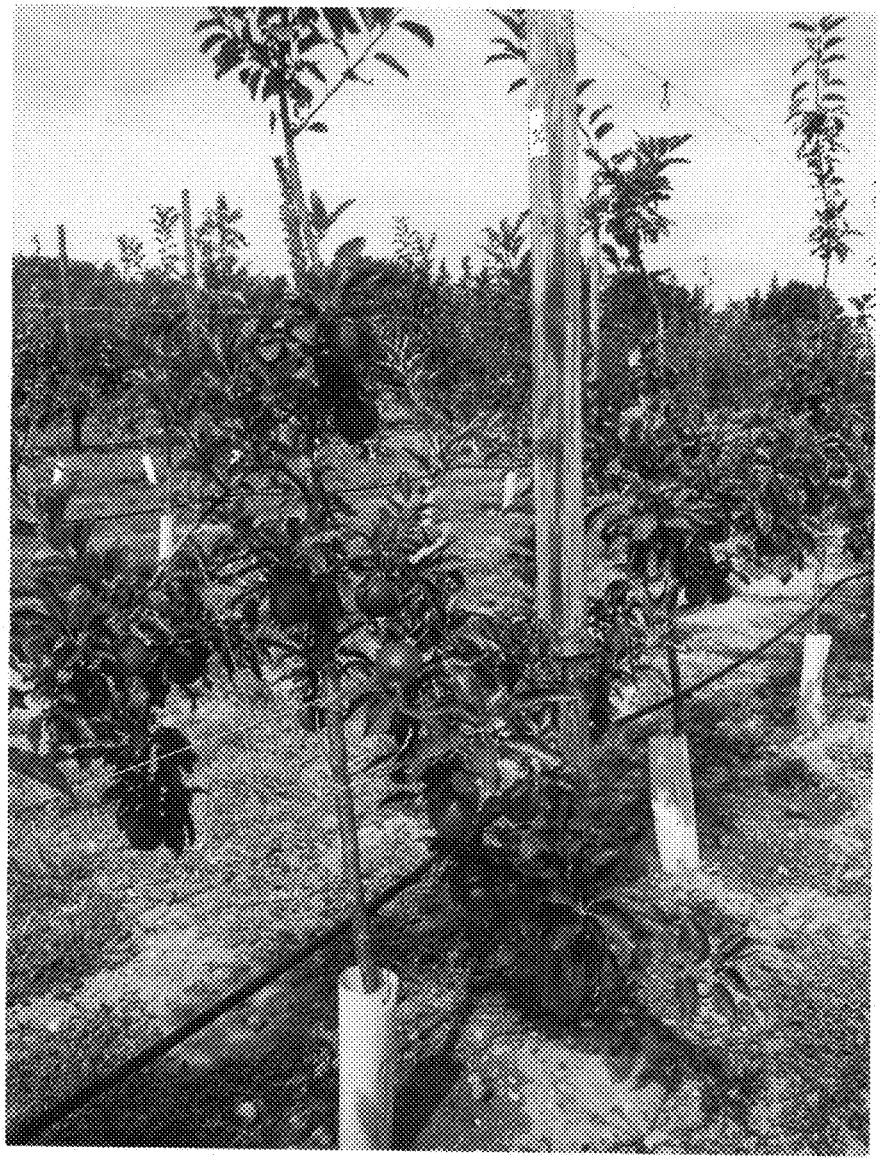
Figure 3:
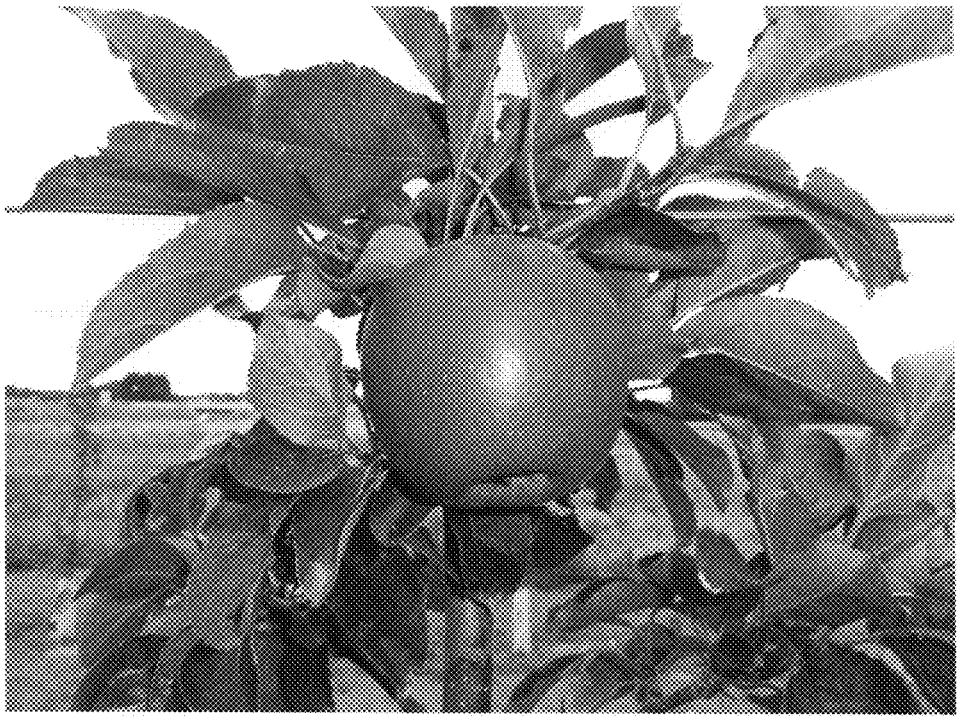
Figure 4:
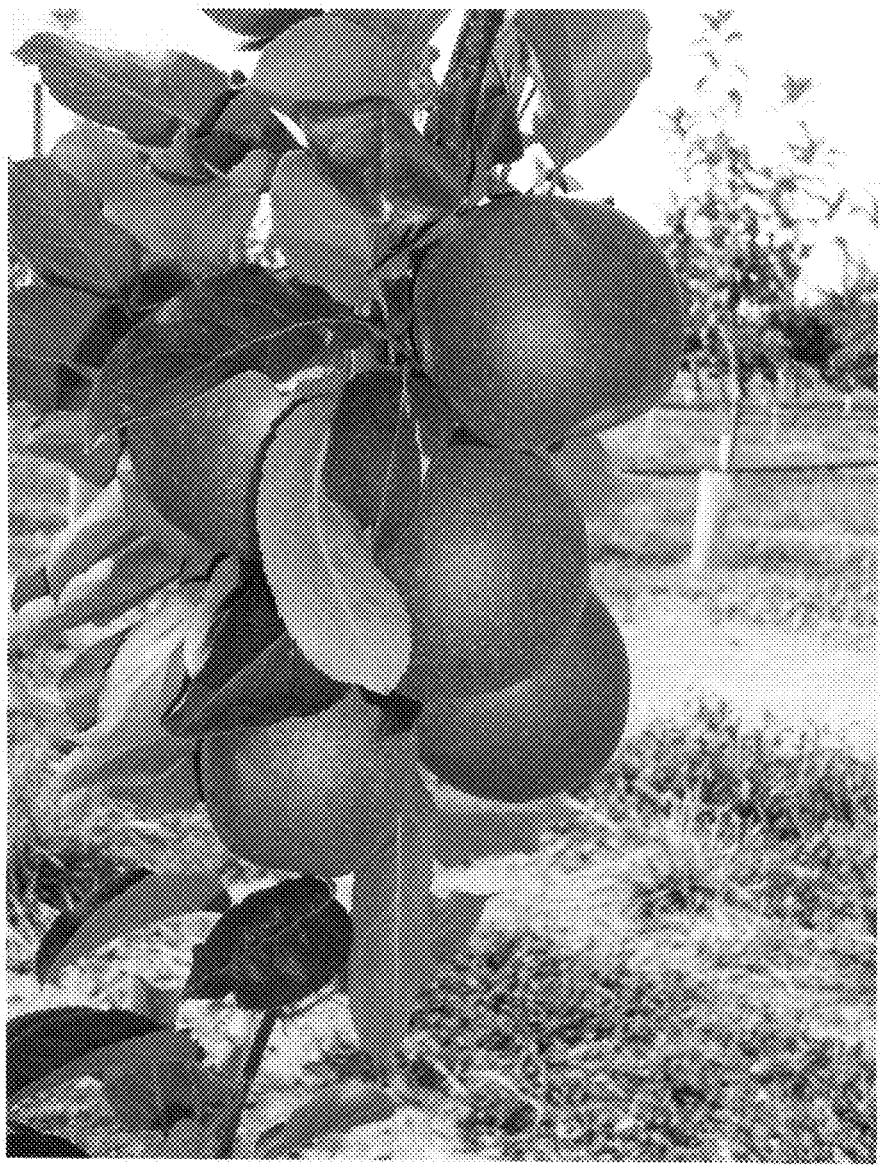

FIGS. 1 and 2 show trees of 'Galafab'; and,
FIGS. 3 and 4 show fruit and leaves of 'Galafab'.

DETAILED BOTANICAL DESCRIPTION OF THE VARIETY

The following-detailed botanical description is based on observations made during the 2013 growing season at Béziers, France, of three-year-old trees planted in 2010 and grown on 'M9 EMLA' rootstock (not patented). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. Colors are described with reference to The R.H.S. Colour Chart.

Tree:

*Vigor.*—Medium.
*Type.*—Ramified.
*Bearing.*—On shoots and spurs.
*Habit.*—Spreading.
*Height.*—Medium small, 3 m.
*Spread.*—1.4 m.
*Trunk diameter* (*at* 30 *cm above the graft*).—Medium (16 to 20 cm).
*Bark texture.*—Smooth.

*Bark color.*—Grey 201D.

Branch (fruiting branches located at around 1 m above the graft union):

*Length.*—Medium, 98 cm from trunk to tip (primary branch).

*Diameter.*—Medium, 2.5 cm at 10 cm from trunk.

*Crotch angle.*—Wide.

*Bark color.*—Light Grey.

*Internode length.*—3.5 cm.

*Lenticel length.*—Medium long.

*Lenticel color.*—Black.

*Number of lenticels per cm$^2$.*—Numerous.

One year old shoot:

*Length.*—30 to 40 cm.

*Color.*—Brown 200B.

*Pubescence.*—Weak.

*Thickness.*—Medium.

*Internode length.*—Medium.

*Number of lenticels per cm$^2$.*—Many.

Leaves:

*Shape.*—Elliptic.

*Length.*—Long, 11 cm.

*Width.*—Medium, 5 cm.

*Length/width ratio.*—Large.

*Blade margin.*—Crenate, finely serrate.

*Apex.*—Pointed.

*Base shape.*—Cuneate.

*Color of upper surface.*—Green 141B.

*Color of lower surface.*—Green 139C.

*Attitude in relation to shoot.*—Upwards.

Petiole:

*Length.*—Medium, 3 to 4 cm.

*Diameter.*—3 mm.

*Coloration.*—Green 139D with Red-purple 59C.

Flower buds:

*Shape.*—Triangular, pointed.

*Length.*—1.8 to 2.4 cm.

*Diameter.*—1.6 to 2.0 cm.

*Color at balloon stage.*—Red-purple 74C.

Flowers:

*Diameter of fully open flower.*—Medium (4.0 to 4.5 cm).

*Relative position of petal margin.*—Free.

*Number per cluster.*—6.

*Date of first bloom.*—April 1$^{st}$.

*Date of full bloom.*—April 5$^{th}$.

*Pollination requirement.*—Similar to Gala.

Petals:

*Number per flower.*—5 (simple row).

*Shape.*—Ovoid.

*Length.*—1.8 cm.

*Width.*—1.4 cm.

*Apex.*—Round.

*Base.*—Elongated.

*Margin.*—Smooth.

*Color of upper surface.*—White 155D, slightly veined red-purple 69C.

*Color of lower surface.*—White 155D, slightly veined red-purple 70D.

Pistils:

*Size.*—1.1 cm.

*Color.*—Green/yellow.

Stigma:

*Size.*—Prominent.

*Color.*—Yellow.

*Position relative to anthers.*—Above anthers.

Style:

*Size.*—1.1 cm.

*Color.*—Green/yellow (pubescent).

Ovary:

*Size.*—0.3×0.3 cm.

*Color.*—Green.

Anthers:

*Quantity.*—18 (one distinct whorl).

*Size.*—0.6 cm to 0.8 cm.

*Presence of pollen.*—Yes.

*Color of pollen.*—Yellow.

Pedicel of flower:

*Length.*—2.2 to 2.6 cm.

*Diameter.*—0.1 to 0.2 cm.

*Color.*—Green 139D.

Sepals:

*Quantity.*—5.

*Length.*—9 mm.

*Color.*—Greyed-green 191C with white pubescence.

*Shape.*—Elongated/pointed.

*Margin.*—Pointed.

Fruit:

*Quantity per cluster.*—3 to 4.

*Diameter.*—Medium (6.5 to 7.5 cm).

*Height.*—Medium (6.5 to 7.5 cm).

*Weight.*—Medium (167 g to 210 g).

*Ratio of height to width.*—1:1.

*General shape in profile.*—Truncate conical.

*Position of maximum diameter.*—Toward stalk.

*Ribbing.*—Moderate.

*Crowning at calyx end.*—Moderate.

*Size of eye.*—Medium.

*Aperture of eye.*—Closed.

*Length of sepal.*—Long.

*Bloom of skin.*—Absent or very weak.

*Greasiness of skin.*—Absent or very weak.

*Background color of skin.*—Yellow 8C.

*Over color of skin.*—Red-purple 59A.

*Amount of over color.*—90% to 100%.

*Intensity of over color.*—Intense.

*Pattern of over color.*—Solid flush.

*Progression of over color before harvest.*—30 days — 50% to 75% drab red; 15 days — 75% to 100% drab red; 5 days — 90% to 100% bright red.

*Amount of russet around stalk cavity.*—Low.

*Amount of russet on cheeks.*—Absent or very low.

*Area of russet around eye basin.*—Absent or very low.

*Lenticles.*—Size — medium; quantity — medium.

*Length of stalk.*—Long, 1 to 2 cm.

*Thickness of stalk.*—Medium.

*Depth of stalk cavity.*—Deep, 1.5 cm.

*Width of stalk cavity.*—Medium, 3.0 to 3.4 cm.

*Depth of eye basin.*—Deep.

*Width of eye basin.*—Medium.

*Firmness of flesh.*—Medium.

*Flesh texture.*—Juicy, fine, crisp.

*Aperture of locules.*—Moderately open.

*Aroma.*—Aromatic, Gala-type aroma.

*Juiciness.*—Moderately juicy.

*Brix.*—13°.

*Flesh coloration.*—Yellowish 11C.

*Stem coloration.*—Greyed-purple 187C.

Seeds:

*Quantity per fruit.*—7 to 9.

*Shape.*—Elongated ovoid.

*Coloration.*—Brown 200C.

Harvest:

*Time for harvest.*—10 August (2013 growing season).

*Number of picks.*—3.

*Amount of fruit produced per tree per harvest.*—68 to 118.

*Weight.*—176 grams.

Disease resistance/susceptibility: Same as Gala.

Cold hardiness: USDA Zone 8/9.

Market use: Fresh Market.

I claim:

1. A new and distinct apple tree named 'Galafab' substantially as illustrated and described herein.

* * * * *